United States Patent [19]
Hauser et al.

[11] Patent Number: 5,843,963
[45] Date of Patent: Dec. 1, 1998

[54] BENZOTHIOPHENE COMPOUNDS, INTERMEDIATES, PROCESSES, COMPOSITIONS, AND METHODS

[75] Inventors: Kenneth Lee Hauser, Greencastle; Alan David Palkowitz, Carmel; Kenneth Jeff Thrasher, Indianapolis, all of Ind.

[73] Assignee: Eli Lilly and Company, Indianapolis, Ind.

[21] Appl. No.: 933,800

[22] Filed: Sep. 19, 1997

Related U.S. Application Data

[60] Provisional application No. 60/026,556 Sep. 24, 1996.

[51] Int. Cl.$^6$ ............ A61K 31/445; C07D 333/64; C07D 409/10
[52] U.S. Cl. ............ 514/324; 514/146; 514/233.5; 514/442; 514/443; 540/596; 544/146; 546/202; 548/525; 549/51
[58] Field of Search ............ 540/596; 544/146; 546/202; 548/525; 549/51; 514/146, 233.5, 324, 442, 443

[56] References Cited

U.S. PATENT DOCUMENTS

| | | | |
|---|---|---|---|
| 3,394,125 | 7/1968 | Crenshaw | 548/525 |
| 3,413,305 | 11/1968 | Crenshaw | 548/525 |
| 4,133,814 | 1/1979 | Jones et al. | 546/202 |
| 4,157,399 | 6/1979 | Sauter | 546/202 |
| 4,230,862 | 10/1980 | Suarez et al. | 546/237 |
| 4,358,593 | 11/1982 | Jones et al. | 546/202 |
| 4,380,635 | 4/1983 | Peters | 546/202 |
| 4,418,068 | 11/1983 | Jones et al. | 546/237 |
| 5,395,842 | 3/1995 | Labrie | 514/320 |
| 5,470,854 | 11/1995 | Angerer et al. | 514/233 |
| 5,472,962 | 12/1995 | Koizumi et al. | 514/233.5 |

FOREIGN PATENT DOCUMENTS

| | | |
|---|---|---|
| 062 503 | 10/1982 | European Pat. Off. . |
| WO 89/0289 | 4/1989 | WIPO . |
| WO 95/10513 | 4/1995 | WIPO . |

OTHER PUBLICATIONS

Crenshaw, R.R., et al, *J. Med. Chem.* 14(12):1185–1190 (1971).
Jones, C.D., et al, *J. Med. Chem.* 27: 1057–1066 1984.
Jones, C.D., et al, *J. Med. Chem.* 35: 931–938 1992.

*Primary Examiner*—Ceila Chang
*Attorney, Agent, or Firm*—Janelle D. Strode; David E. Boone

[57] ABSTRACT

The invention provides benzothiophene compounds, of formula I,

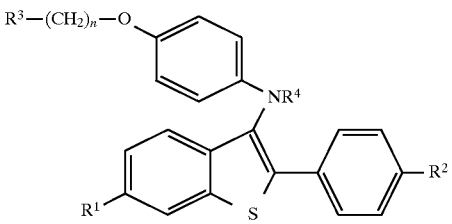

wherein R1, R2, R3, R4 and n are as defined in the specification, formulations, and methods of inhibiting bone loss or bone resorption, particularly osteoporosis, and cardiovascular-related pathological conditions, including hyperlipidemia, and other cardiovascular pathologies.

13 Claims, No Drawings

BENZOTHIOPHENE COMPOUNDS, INTERMEDIATES, PROCESSES, COMPOSITIONS, AND METHODS

BACKGROUND OF THE INVENTION

This application is based on a provisonal application 60/026,556 filed Sep. 24, 1996.

Osteoporosis describes a group of diseases which arises from diverse etiologies, but which are characterized by the net loss of bone mass per unit volume. The consequence of this loss of bone mass and resulting bone fracture is the failure of the skeleton to provide adequate support for the body. One of the most common types of osteoporosis is associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among postmenopausal women.

There are an estimated 25 million women in the United States alone who are afflicted with this disease. The results of osteoporosis are personally harmful, and also account for a large economic loss due to its chronicity and the need for extensive and long term support (hospitalization and nursing home care) from the disease sequelae. This is especially true in more elderly patients. Additionally, although osteoporosis is generally not thought of as a life threatening condition, a 20% to 30% mortality rate is related to hip fractures in elderly women. A large percentage of this mortality rate can be directly associated with postmenopausal osteoporosis.

The most vulnerable tissue in the bone to the effects of postmenopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which interconnect with each other, as well as the more solid and dense cortical tissue which makes up the outer surface and central shaft of the bone. This interconnected network of trabeculae gives lateral support to the outer cortical structure and is critical to the biomechanical strength of the overall structure. In postmenopausal osteoporosis, it is primarily the net resorption and loss of the trabeculae which leads to the failure and fracture of bone. In light of the loss of the trabeculae in the postmenopausal woman, it is not surprising that the most common fractures are those associated with bones which are highly dependent on trabecular support, for example, the vertebrae, the neck of the weight-bearing bones such as the femur and the forearm. Indeed, hip fracture, collies fractures, and vertebral crush fractures are hallmarks of postmenopausal osteoporosis.

The most generally accepted method for the treatment of postmenopausal osteoporosis is estrogen replacement therapy. Although therapy is generally successful, patient compliance with the therapy is low, primarily because estrogen treatment frequently produces undesirable side effects. An additional method of treatment would be the administration of a bisphosphonate compound, such as, for example, Fosamax® (Merck & Co., Inc.).

Throughout premenopausal time, most women have less incidence of cardiovascular disease than men of the same age. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can up regulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that serum lipid levels in postmenopausal women having estrogen replacement therapy return to concentrations found in the premenopausal state. Thus, estrogen would appear to be a reasonable treatment for this condition. However, the side effects of estrogen replacement therapy are not acceptable to many women, thus limiting the use of this therapy. An ideal therapy for this condition would be an agent which regulates serum lipid levels in a manner analogous to estrogen, but which is devoid of the side effects and risks associated with estrogen therapy.

The instant invention provides benzo[b]thiophene compounds, pharmaceutical formulations thereof, and methods of using such compounds for inhibiting the above-mentioned pathologies.

SUMMARY OF THE INVENTION

The present invention relates to compounds of formula I

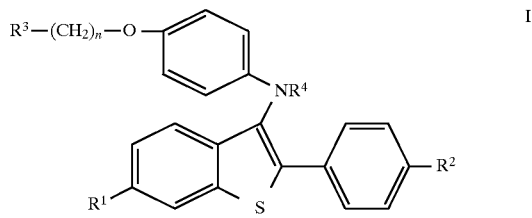

wherein:

$R^1$ is —H, —OH, —O($C_1$–$C_4$ alkyl), —OCOAr, —O(CO)OAr, where Ar is phenyl or substituted phenyl, —OCO($C_1$–$C_6$ alkyl), —O(CO)O($C_1$–$C_6$ alkyl), or —OSO$_2$($C_2$–$C_6$ alkyl);

$R^2$ is —H, —Cl, —F, —OH, —O($C_1$–$C_4$ alkyl), —OCOAr, —O(CO)OAr, where Ar is phenyl or substituted phenyl, —OCO($C_1$–$C_6$ alkyl), —O(CO)O ($C_1$–$C_6$ alkyl), or —OSO$_2$($C_2$–$C_6$ alkyl);

$R^3$ is 1-piperidinyl, 1-pyrrolidinyl, methyl-1-pyrrolidinyl, dimethyl-1-pyrrolidinyl, 4-morpholino, dimethylamino, diethylamino, diisopropylamino, or 1-hexamethyleneimino;

$R^4$ is —H, $C_1$–$C_5$ alkyl, —COAr, —(CO)H, —CO($C_1$–$C_6$ alkyl), —SO$_2$($C_2$–$C_6$ alkyl), or —SO$_2$Ar, where Ar is phenyl or substituted phenyl; and n is 2 or 3;

or a pharmaceutically acceptable salt or solvate thereof.

Also provided by the present invention are intermediate compounds of formula II which are useful for preparing the pharmaceutically active compounds of the present invention, and are shown below:

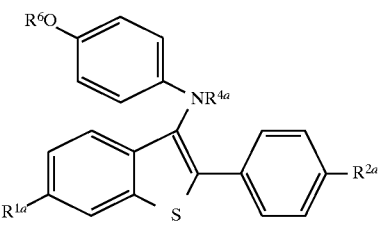

II wherein:
$R^{1a}$ is —H or —$OR^7$ in which $R^7$ is a hydroxy protecting group;
$R^{2a}$ is —H, —Cl, —F, or —$OR^7$ in which $R^7$ is a hydroxy protecting group;
$R^{4a}$ is —CO($C_1$–$C_4$ alkyl) or —(CO)H; and
$R^6$ is —H or $R^8$, wherein $R^8$ is a hydroxy protecting group which can be selectively removed in the presence of —$OR^7$.

Further, the present invention provides compounds of formula VII, which are useful for the synthesis of the compounds of formula I:

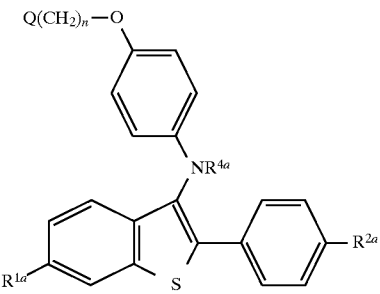

VII wherein:
$R^{1a}$, $R^{2a}$, $R^{4a}$, and n have their previous meanings and Q is a leaving group.

The present invention further relates to pharmaceutical formulations containing compounds of formula I, and the use of such compounds for alleviating the symptoms of bone loss or bone resorption, particularly osteoporosis, cardiovascular-related pathological conditions, and the like.

DETAILED DESCRIPTION OF THE INVENTION

General terms used in the description of compounds herein described bear their usual meanings. For example, "$C_1$–$C_6$ alkyl" refers to straight or branched aliphatic chains of 1 to 6 carbon atoms including methyl, ethyl, propyl, isopropyl, butyl, n-butyl, pentyl, isopentyl, hexyl, isohexyl, and the like. Similarly, the term "—$OC_1$–$C_4$ alkyl" represents a $C_1$–$C_4$ alkyl group attached through an oxygen such as, for example, methoxy, ethoxy, n-propoxy, isopropoxy, and the like. Of these $C_1$–$C_4$ alkoxy groups, methoxy is highly preferred.

The term "substituted phenyl" refers to a phenyl group having one or more substituents selected from the group consisting of $C_1$–$C_4$ alkyl, —$OC_1$–$C_4$ alkyl, hydroxy, nitro, chloro, fluoro, or tri(chloro or fluoro)methyl.

The term "hydroxy protecting group" contemplates numerous functionalities used in the literature to protect a hydroxyl function during a chemical sequence and which can be removed to yield the phenol. Included within this group would be acyls, mesylates, tosylates, benzyl, alkylsilyloxys, $C_1$–$C_4$ alkyls, and the like. Numerous reactions for the formation and removal of such protecting groups are described in a number of standard works including, for example, Protective Groups in Organic Chemistry, Plenum Press (London and New York, 1973); Green, T. W., Protective Groups in Organic Synthesis, Wiley, (New York, 1981); and The Peptides, Vol. I, Schrooder and Lubke, Academic Press (London and New York, 1965). Methods for removing preferred $R^7$ hydroxy protecting groups, particularly methyl and alkylsilyloxy, are essentially as described in the Examples, infra.

The term "leaving group (Q)" means a chemical entity which is capable of being displaced by an amino function via an $SN_2$ reaction. Such reactions are well known in the art and such groups would include halogens, mesylates, tosylates, and the like. A preferred leaving group would be bromo.

The term "inhibit" includes its generally accepted meaning which includes prohibiting, preventing, restraining, and slowing, stopping, or reversing progression, severity, or ameliorating a resultant symptom or effect.

The term "solvate" represents an aggregate that comprises one or more molecules of the solute, such as a formula I compound, with one or more molecules of solvent.

The compounds of this invention are derivatives of centrally located carbon, for example, the "—CO—", "—CHOH—", or "—$CH_2$—" moiety in formula I are therefore derivatives of methanones, methanols, or methanes. For example, a compound of A-CO-B, would be named [A][B] methanone. Further, the compounds of formula I are derivatives of benzo[b]thiophene which is named and numbered according to the Ring Index, The American Chemical Society, as follows:

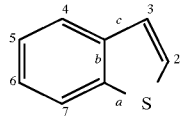

Preferred compounds of the present invention are 2-(4-hydroxyphenyl)-3-[N-[4-[2-(1-piperidinyl)ethoxy]phenyl]amino]-6-hydroxybenzo[b]thiophene hydrochloride and 2-(4-methoxyphenyl)-3-[N-[4-[2-(1-piperidinyl)ethoxy]phenyl]amino]- 6-methoxybenzo[b]thiophene di-hydrochloride.

Several synthetic pathways are available for preparing the compounds of the instant invention. The first synthetic route is illustrated in Scheme I, below. The starting material for one route for preparing compounds of formula I of the present invention, compounds of formula III, are prepared essentially as described by Jones et al. in U.S. Pat. Nos. 4,418,068, and 4,133,814, the disclosures of which are herein incorporated by reference. Formula III has the following structure:

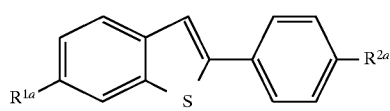

III wherein $R^{1a}$ and $R^{2a}$ are as defined above.

For compounds of formula III, a preferred $R^7$ substituent is methyl or methoxymethyl. Compounds in which $R^{1a}$ and $R^{2a}$ each are methoxy, as well as other derivatives, are prepared via the procedure described in Jones et al., supra.

The first steps of the present process for preparing certain compounds of formula I include selectively placing a leaving group at the 3 position of a formula III compound, coupling the reaction product of the first step with a 4-(protected-hydroxy)phenylacylamide (formula V), and removing the hydroxy protecting group to generate a phenol of compound IIb. The process is depicted in Scheme I below.

II compound. A preferred $R^8$ protecting group is benzyl. The 4-(protected-hydroxy)phenylalkylamides are known compounds and can be prepared via standard procedures. For example, a preferred reagent, for example,

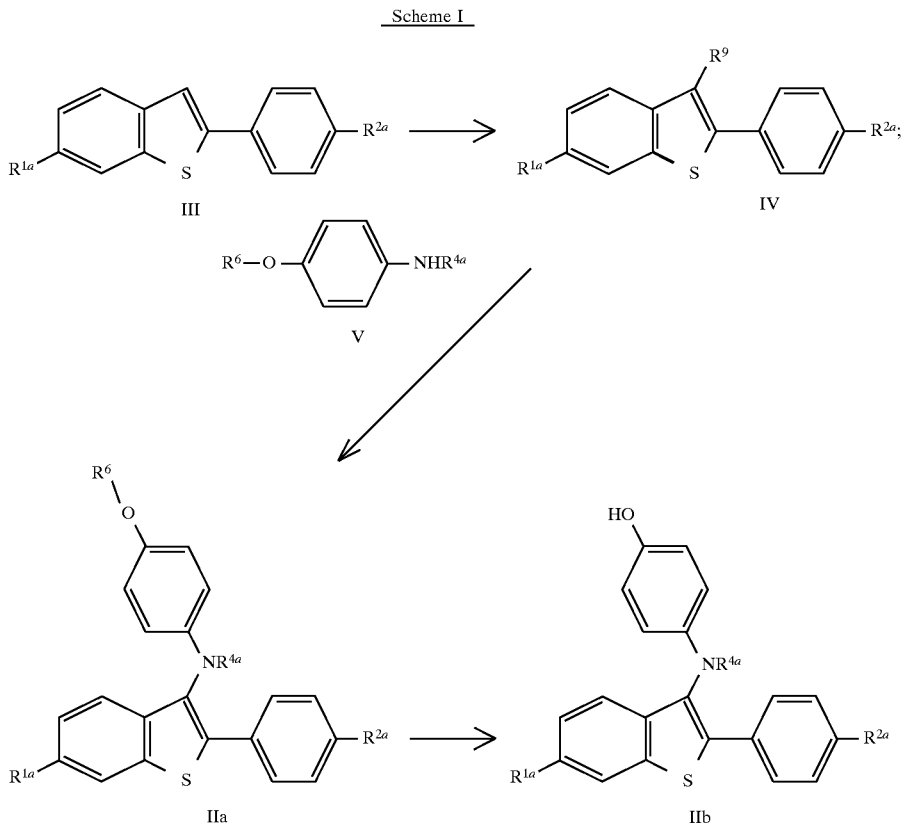

Scheme I 4-benzyloxyphenyl acetamide, may be synthesized from commercially available 4-benzyloxyaniline and acetic anhydride by methods known in the art.

In the first step of Scheme I, an appropriate leaving group is selectively placed at the 3-position of the formula III starting material via standard procedures. Appropriate $R^9$ leaving groups include sulfonates such as methanesulfonate, 4-bromobenzenesulfonate, toluenesulfonate, ethanesulfonate, isopropanesulfonate, 4-methoxybenzenesulfonate, 4-nitrobenzenesulfonate, 2-chlorobenzenesulfonate, triflate, and the like, halogens such as bromo, chloro, and iodo, and other related leaving groups. However, to insure proper placement of the leaving group, the named halogens are preferred, and bromo is especially preferred.

The present reaction is carried out using standard procedures. For example, when the preferred halogenating agents are used, an equivalent of such a halogenating agent, preferably bromine, is reacted with an equivalent of the formula III substrate, in the presence of a suitable solvent such as, chloroform or acetic acid. The reaction is run at a temperature from about 400° C. to about 80° C. and is usually complete in one to six hours.

The reaction product from the above process step, a compound of formula IV, is then reacted with a 4-(protected-hydroxy)phenylakylamide (formula V), for example, in which $R^{4a}$ is —(CO)H or —CO($C_1$–$C_4$ alkyl), to form compounds of formula II in which $R^8$ is a selectively-removable hydroxy protecting group. Generally, the 4-hydroxy protecting moiety of the phenol may be any known protecting group which can be selectively removed without removing the $R^7$, when present, moiety of a formula This coupling reaction of IV and V is known in the art as an Ullman-type reaction, and various standard procedures are listed. [See, for example, Advanced Organic Chemistry: Reactions, Mechanisms, and Structure, Fourth Edition, 3–16, (J. March, ed., John Wiley & Sons, Inc. 1992); Jones, C. D., J. Chem. Soc. Perk. Trans. I, 4:407 (1992)].

Although several variations of the standard Ullman-type reactions were attempted, for example, reacting an aniline or an anilinosulfamide with aryl bromide in the presence of a copper catalyst, only a variant known as a Goldberg reaction was successful. Details of this reaction are given below.

In general, equivalent amounts of the two aryl substrates, in the presence of up to an equimolar amount of a copper(I) oxide catalyst and an appropriate solvent, are heated to reflux under an inert atmosphere. Examples of a suitable catalytic copper (I) salt would include but not be limited to $Cu_2O$, CuI, and $Cu_2CO_3$. Preferably, an equivalent of a formula IV compound in which $R^9$ is bromo is reacted with an equivalent amount of 4-benzyloxyphenylacetamide in the presence of an equivalent of cuprous oxide.

Appropriate solvents for this reaction are those solvents or mixture of solvents which remain inert throughout the reaction. Typically, organic bases, particularly a hindered base such as, for example, 2,4,6-collidine, are preferred solvents.

The temperature employed in this step should be sufficient to effect completion of this coupling reaction, and will influence the amount of time required therefor. When the reaction mixture is heated to reflux under an inert atmosphere such as nitrogen. The reaction is usually complete in twenty to one hundred-twenty hours.

Following the coupling reaction, which forms a formula IIa compound, formula IIb compounds are prepared, via well known reduction procedures, by selectively removing the $R^6$ hydroxy protecting group. It is imperative that the selected procedure will not affect, when present, the $R^7$ hydroxy protecting group.

When $R^8$ is the preferred benzyl moiety, and $R^7$, when present, is methyl, the present process step is carried out via standard hydrogenolysis procedures. Typically, the formula IIa substrate is added to a suitable solvent or mixture of solvents, followed by the addition of a proton donor to accelerate the reaction and an appropriate hydrogenation catalyst.

Appropriate catalysts include noble metals and oxides such as palladium, platinum, and rhodium oxide on a support such as carbon or calcium carbonate. Of these, palladium-on-carbon, particularly 10% palladium-on-carbon, is preferred.

Solvents for this reaction are those solvents or mixture of solvents which remain inert throughout the reaction. Typically, ethylacetate and $C_1$–$C_4$ aliphatic alcohols, particularly ethanol, is preferred.

For the present reaction, hydrochloric acid serves as an adequate and preferred proton donor.

When run at ambient temperature and at a hydrogen pressure ranging from about 30 psi to about 50 psi, the present reaction runs quite rapidly. Progress of this reaction may be monitored by standard chromatographic techniques such as thin layer chromatography.

Compounds of formula IIa and IIb are encompassed within the genus described herein as formula II compounds, and are useful for preparing the pharmaceutically active compounds of formula I.

Examples of the compounds of formula II include:

2-(4-methoxyphenyl)-3-[N-(4-hydroxyphenyl)acetamido]-6-methoxy-benzo[b]thiophene 2-phenyl-3-[N-(4-hydroxyphenyl)acetamido]-6-methoxy-benzo[b]thiophene 2-(4-fluorophenyl)-3-[N-(4-hydroxyphenyl)acetamido]-6-methoxy-benzo[b]thiophene 2-(4-chlorophenyl)-3-[N-(4-hydroxyphenyl)acetamido]-6-methoxy-benzo[b]thiophene 2-(4-methoxyphenyl)-3-[N-(4-benzyloxyphenyl)acetamido]-6-methoxy-benzo[b]thiophene 2-phenyl-3-[N-(4-benzyloxyphenyl)acetamido]-6-methoxy-benzo[b]thiophene 2-(4-methoxyphenyl)-3-[N-(4-hydroxyphenyl)propanoylamido]-6-methoxy-benzo[b]thiophene 2-(4-methoxyphenyl)-3-[N-(4-benzyloxyphenyl)butanoylamido]-6-methoxy-benzo[b]thiophene 2-(4-chorophenyl)-3-[N-(4-benzyloxyphenyl)acetamido]benzo[b]thiophene 2-(4-methoxyphenyl)-3-[N-(4-hydroxyphenyl)acetamido]benzo[b]thiophene 2-(4-methoxyphenyl)-3-[N-(4-benzyloxyphenyl)acetamido]benzo[b]thiophene 2-(4-methoxyphenyl)-3-[N-(4-benzyloxyphenyl)formylamido]benzo[b]thiophene 2-(4-fluorophenyl)-3-[N-(4-benzyloxyphenyl)propanoylamido]benzo[b]thiophene, and the like.

The compounds of formula IIb may be converted into the compounds of formula Ia by one of two different synthetic routes, which are illustrated in Scheme II, below.

The first method is the direct conversion of IIb to Ia by using a reagent of formula VI:

$$R^3\text{—}(CH_2)_n\text{—}Q$$

wherein $R^3$ and n are as defined above, and Q is a leaving group, such as a bromo or chloro moiety.

Scheme II

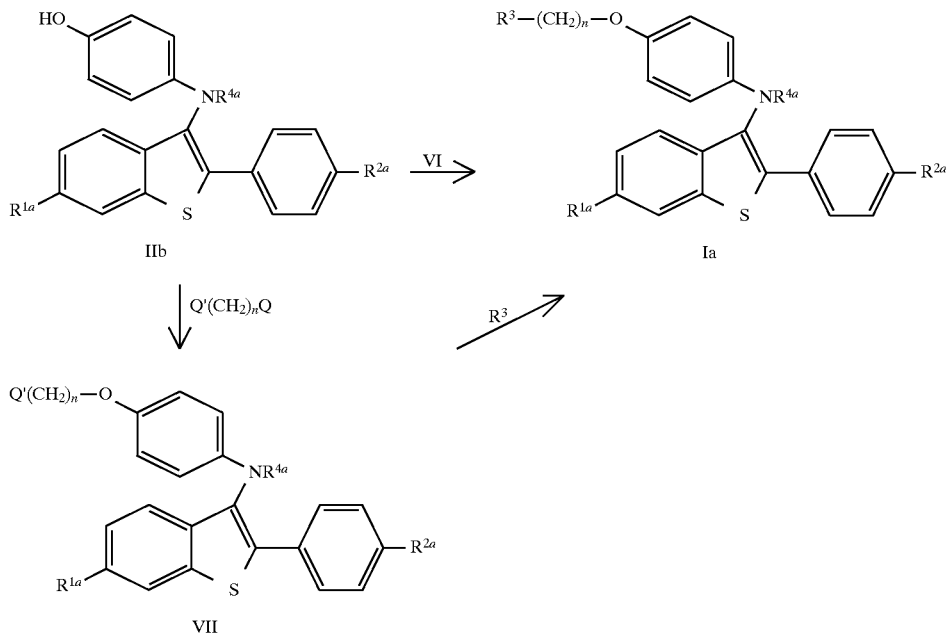

The direct alkylation process, shown in Scheme II, is carried out via standard procedures. Compounds of formula VI are commercially available or are prepared by means well known to one of ordinary skill in the art. Preferably, the hydrochloride salt of a formula VI compound, particularly preferred is 2-chloroethylpiperidine hydrochloride.

Generally, at least about 1 equivalent of formula IIb substrate are reacted with 2 equivalents of a formula VI compound in the presence of at least about 4 equivalents of an alkali metal carbonate, preferably cesium carbonate, and an appropriate solvent.

Solvents for this reaction are those solvents or mixtures of solvents which remain inert throughout the reaction. N,N-dimethylformamide, especially the anhydrous form thereof, is preferred.

The temperature employed in this step should be sufficient to effect completion of this alkylation reaction. Typically, ambient temperature is sufficient and preferred.

The present reaction preferably is run under an inert atmosphere, particularly nitrogen.

Under the preferred reaction conditions, this reaction will run to completion in about 16 to about 20 hours. Of course, the progress of the reaction can be monitored via standard chromatographic techniques.

The second method for preparing compounds of formula Ia from a formula IIb compound is to proceed through an intermediate compound (formula VII) in a two-step sequence (see Scheme II, supra). A compound of formula IIb is reacted with an excess of an alkylating agent of the formula Q—(CH$_2$)$_n$—Q' wherein Q and Q' each are the same or different leaving groups, in an alkali solution. Appropriate leaving groups can be, for example, chloro, bromo, mesylates, tosylates and the like. A preferred alkali solution for this alkylation reaction contains potassium carbonate in an inert solvent such as, for example, methylethyl ketone (MEK) or DMF. In this solution, the 4-hydroxy group of the phenyl moiety of a formula IIb compound exists as a phenoxide ion which displaces one of the leaving groups of the alkylating agent.

This reaction proceeds rapidly when the alkali solution containing the reactants and reagents is brought to reflux and allowed to run to completion. When using MEK as the preferred solvent, reaction times run from about 6 hours to about 20 hours.

The compounds of formula VII are useful in the synthesis of the compounds of formula I. Compounds of formula VII would include:

2-(4-methoxyphenyl)-3-[N-[4-(2-bromoethoxy)phenyl] acetylamido]-6-methoxybenzo[b]thiophene 2-phenyl-3-[N-[4-(2-bromoethoxy)phenyl]acetylamido]-6-methoxybenzo[b]thiophene 2-(4-methoxyphenyl)-3-[N-[4-bromoethoxy)phenyl] acetylamido]benzo[b]thiophene 2-(4-methoxyphenyl)-3-[N-[4-(2-bromopropoxy)phenyl] acetylamido]-6-methoxybenzo[b]thiophene 2-(4-methoxyphenyl)-3-[N-[4-(2-chloroethoxy)phenyl] acetylamido]-6-methoxybenzo[b]thiophene 2-(4-methoxyphenyl)-3-[N-[4-(2-tosylethoxy)phenyl] acetylamido]-6-methoxybenzo[b]thiophene 2-(4-methoxyphenyl)-3-[N-[4-(2-bromoethoxy)phenyl] butanoylamido]-6-methoxybenzo[b]thiophene 2-(4-methoxyphenyl)-3-[N-[4-(2-bromoethoxy)phenyl] formylamido]-6-methoxybenzo[b]thiophene, and the like.

The reaction product (formula VII) from this step is then reacted with an amine (R$^3$), for example, 1-piperidine, 1-pyrrolidine, methyl-1-pyrrolidine, dimethyl-1-pyrrolidine, 4-morpholine, dimethylamine, diethylamine, diisopropylamine, or 1-hexamethyleneimine, via standard techniques, to form compounds of formula Ia. Preferably, the hydrochloride salt of piperidine is reacted with a compound of formula VII in an inert solvent, such as anhydrous DMF, and heated to a temperature in the range from about 60° C. to about 110° C. When the mixture is heated to a preferred temperature of about 90° C., the reaction only takes about 30 minutes to about 1 hour. However, changes in the reaction conditions will influence the amount of time this reaction needs to be run for completion. Of course, the progress of this reaction step may be monitored via standard chromatographic techniques.

Conversion of the compounds of formula Ia to other compounds of formula I is shown in Scheme III and may involve: the removal of the N-acyl group to form the di-aryl amino series (Ib), removal and re-introduction to form another acyl or a sulfonyl series (Ic), or the reduction of the N-acyl to a N-alkyl series (Id).

Scheme III

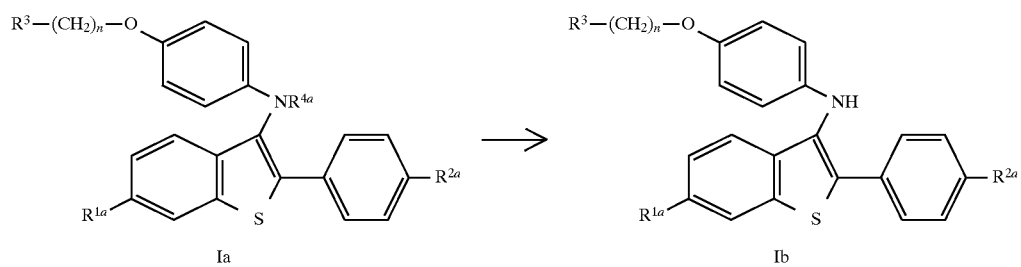

-continued
Scheme III

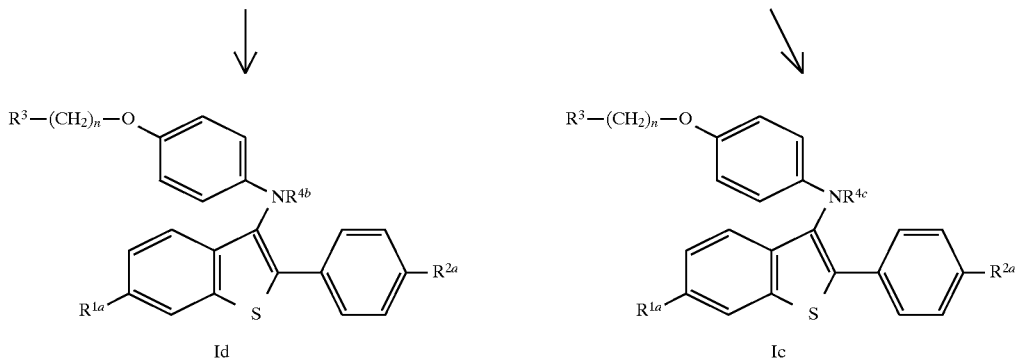

Id

Ic

Removal of the N-acyl group from a compound of formula Ia can readily be accomplished by either acid or base hydrolysis to form a compound of Ib, where $R^{1a}$, $R^{2a}$, $R^3$, and n have their previous meanings. The preferred method involves heating a formula Ia compound in a solution of alcohol and concentrated alkoxide. Typically, EtOH is used as the organic solvent and 50% NaOH solution is used as the source of base. The substrate is dissolved in an equal mixture of the alcohol and base and heated to the reflux temperature of the combined solvent. The reaction usually requires between 6 and 24 h for completion.

Compounds of formula Ib are pharmaceutically active for the methods herein described. Accordingly, such compounds are encompassed by the definition herein of compounds of formula I.

Additionally, compounds of formula Ib may serve as substrates for preparing compounds of formula Ic where $R^{1a}$, $R^{2a}$, $R^3$, and n have their previous meanings and $R^{4c}$ is —$CO(C_1$–$C_6$ alkyl), —(CO)H, —COphenyl, —$SO_2$phenyl, or —$SO_2(C_2$–$C_6$alkyl). To form these compounds, the nitrogen is either acylated or sulfonated. This can readily be accomplished by a variety of acylation and alkylation methods that are well known in the art. For further methods on such acylations and sulfonations, the discussion on derivatization of the phenols (see below) is applicable.

The compounds of formula Ia may also be converted to the compounds of formula Id, where $R^{1a, R2a}$, $R^3$, and n have their previous meanings and $R^{4b}$is $C_1$–$C_5$ alkyl. This transformation may be achieved by the reduction of the amide carbonyl in Ia to its corresponding methylene with a reducing reagent such as LAH. These reductions are known in the art and are usually carried out in inert solvents such as anhydrous THF, ether, and the like. These reactions are run with an excess of the reducing reagent and at temperatures of –50° to 30° C. under a nitrogen atmosphere. Reactions are normally complete within two to twenty-four hours, standard techniques such as tic may be used to monitor the extent of the reaction.

The compounds of formula Ia, Ib, Ic, and Id are pharmacologically active for the methods herein described, and are encompassed in formula I as defined herein. Additionally, compounds of formula Ia–d may serve as substrates for other compounds of formula I, such as, for example, compounds where $R^{1a}$ and $R^{2a}$ are converted to $R^1$ and $R^2$, respectively.

Preferred compounds of formula I are obtained by cleaving the $R^7$ hydroxy protecting group, when present, of formulae Ia–d compounds via well known procedures. Numerous reactions for the formation and removal of such protecting groups are described in a number of standard works including, for example, Protective Groups in *Organic Chemistry*, Plenum Press (London and New York, 1973); Green, T. W., Protective Groups in *Organic Synthesis*, Wiley, (New York, 1981); and The Peptides, Vol. I, Schrooder and Lubke, Academic Press (London and New York, 1965). Methods for removing the preferred $R^7$ hydroxy protecting group, methyl, is essentially as described in the Examples, infra Other preferred compounds of formula I are prepared by converting 6- and/or 4'-position hydroxy moieties, when present, to a moiety of the formula —O—CO—($C_1$–$C_6$ alkyl), —$OCOC_6H_5$, —O(CO)O($C_1$–$C_6$ alkyl) or —O—$SO_2$-($C_2$–$C_6$ alkyl) via well known procedures. Such methods are described in U.S. Pat. Nos. 5,393,763 and 5,482,949 the disclosures of which are herein incorporated by reference.

For example, when an —O—CO($C_1$–$C_6$ alkyl) group is desired, a mono- or dihydroxy compound of formula Ia–d is reacted with an agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger (except as noted below), such as a tertiary amine, has been added. If desired, acylation catalysts such as 4-dimethylaminopyridine or 4-pyrrolidinopyridine may be used. See, for example, Haslam, et al., *Tetrahedron*, 36:2409–2433 (1980).

The present reactions are carried out at moderate temperatures, in the range from about –25° C. to about 100° C., frequently under an inert atmosphere such as nitrogen gas. However, ambient temperature is usually adequate for the reaction to run.

Side-reactions of acylating the bis-aryl nitrogen (formula Ib compounds) may be reduced by not using excess amounts of acylating reagent and using lower temperatures. Undesired isomers may be removed by chromatography on silica gel eluted with mixtures of solvents, such as, MeOH-$CHCl_3$ (1:99) (v/v) or EtOAc-hexane mixtures.

Acylation of a 6-position and/or 4'-position hydroxy group also may be performed by acid-catalyzed reactions of the appropriate carboxylic acids in inert organic solvents. Acid catalysts such as sulfuric acid, polyphosphoric acid, methanesulfonic acid, and the like are used.

The aforementioned $R^1$ and/or $R^2$ groups of formula Ia–d compounds also may be provided by forming an active ester of the appropriate acid, such as the esters formed by such known reagents such as dicyclohexylcarbodiimide, acylimidazoles, nitrophenols, pentachlorophenol, N-hydroxysuccinimide, and 1-hydroxybenzotriazole. See, for example, Bull. *Chem. Soc.* Japan, 38:1979 (1965), and *Chem. Ber.*, 788 and 2024 (1970).

Each of the above techniques which provide —O—CO—($C_{1-6}$ alkyl) moieties are carried out in solvents as discussed above. Those techniques which do not produce an acid product in the course of the reaction, of course, do not call for the use of an acid scavenger in the reaction mixture.

When a formula Ia–d compound is desired in which the 6-and/or 4'-position hydroxy group of a formula I compound is converted to a group of the formula —O—$SO_2$—($C_2$-$C_6$ alkyl), the mono- or dihydroxy compound is reacted with, for example, a sulfonic anhydride or a derivative of the appropriate sulfonic acid such as a sulfonyl chloride, bromide, or sulfonyl ammonium salt, as taught by King and Monoir, *J. Am. Chem. Soc.*, 97:2566–2567 (1975). The dihydroxy compound also can be reacted with the appropriate sulfonic anhydride or mixed sulfonic anhydrides. Such reactions are carried out under conditions such as were explained above in the discussion of reaction with acid halides and the like.

The compounds of formula Ia–d, their phenolic hydroxyl compounds, and their corresponding derivatized phenols, combined, constitute the compounds of formula I of the current invention.

Examples of the compounds of formula I include:

2-(4-methoxyphenyl)-3-[N-[4-[2-(1-piperidinyl)ethoxy]phenyl]acetamido]-6-methoxybenzo[b]thiophene 2-(4-hydroxyphenyl)-3-[N-[4-[2-(1-piperidinyl)ethoxy]phenyl]acetamido]-6-hydroxybenzo[b]thiophene 2-(4-methoxyphenyl)-3-[N-[4-[2-(1-piperidinyl)ethoxy]phenyl]acetamido]-6-hydroxybenzo[b]thiophene 2-(4-hydroxyphenyl)-3-[N-[4-[2-(1-piperidinyl)ethoxy]phenyl]amino]-6-methoxybenzo[b]thiophene 2-(4-methoxyphenyl)-3-[N-[4-[2-(1-piperidinyl)ethoxy]phenyl]-N-ethylamino]-6-methoxybenzo[b]thiophene 2-(4-Methoxyphenyl)-3-[N-[4-[2-(1-piperidinyl)ethoxy]phenyl]propanoylamido]-6-methoxybenzo[b]thiophene 2-(4-methoxyphenyl)-3-[N-[4-[2-(1-piperidinyl)ethoxy]phenyl]acetamido]-6-methoxybenzo[b]thiophene 2-(4-methoxyphenyl)-3-[N-[4-[3-(1-piperidinyl)propoxy]phenyl]acetamido]benzo[b]thiophene 2-(4-methoxyphenyl)-3-[N-[4-[2-(1-piperidinyl)ethoxy]phenyl]acetamido]-6-methoxybenzo[b]thiophene 2-(4-methoxyphenyl)-3-[N-[4-[2-(1-pyrrolidinyl)ethoxy]phenyl]amino]-6-methoxybenzo[b]thiophene 2-(4-chlorophenyl)-3-[N-[4-[3-(1-hexamethylene)propoxy]phenyl]butanoylimido]-6-methoxybenzo[b]thiophene 2-phenyl-3-[N-[4-[2-(1-piperidinyl)ethoxy]phenyl]-N-methylamino]benzo[b]thiophene 2-(4-chlorophenyl)-3-[N-[4-[3-(1-pyrrolidinyl)propoxy]phenyl]-N-butylamino]-6-hydroxybenzo[b]thiophene 2-(4-acetyloxyphenyl)-3-[N-[4-[2-(1-piperidinyl)ethoxy]phenyl]acetamido]-6-methoxybenzo[b]thiophene 2-(4-methoxyphenyl)-3-[N-[4-[2-(1-piperidinyl)ethoxy]phenyl]acetamido]-6-n-butylsulfonyloxybenzo[b]thiophene 2-phenyl-3-[N-[4-[2-(1-piperidinyl)ethoxy]phenyl]acetamido]-6-benzoyloxybenzo[b]thiophene 2-(4-benzoyloxyphenyl)-3-[N-[4-[3-(1-piperidinyl)propoxy]phenyl]acetamido]-6-methoxybenzo[b]thiophene 2-(4-benzoyloxyphenyl)-3-[N-[4-[3-(1-hexamethyleneimino)propoxy]phenyl]-N-2-butylamino]-6-methoxybenzo[b]thiophene 2-[4-(4-methoxybenzoyloxy)phenyl]-3-[N-[4-[2-(1-piperidinyl)ethoxy]phenyl]-N-methylamino]-6-methoxybenzo[b]thiophene, and the like.

Although the free-base form of formula I compounds can be used in the methods of the instant invention, it is preferred to prepare and use a pharmaceutically acceptable salt form. The term "pharmaceutically acceptable salt" refers to either acid or base addition salts which are known to be non-toxic and are commonly used in the pharmaceutical literature. The pharmaceutically acceptable salts generally have enhanced solubility characteristics compared to the compound from which they are derived, and thus are often more amenable to formulation as liquids or emulsions. The compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention.

Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl-substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caproate, caprylate, chloride, cinnamate, citrate, formate, fumarate, glycolate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration, or the solvent can be stripped off by conventional means. The instant invention further provides for pharmaceutically acceptable formulations for administering to a mammal, including humans, in need of treatment, which comprises an effective amount of a compound of formula I and a pharmaceutically acceptable diluent or carrier.

As used herein, the term "effective amount" means an amount of compound of the instant invention which is capable of inhibiting, alleviating, ameliorating, treating, or preventing further symptoms in mammals, including humans, suffering from bone loss or bone resorption, particularly osteoporosis, and cardiovascular-related pathological conditions including hyperlipidemia, and other cardiovascular pathologies.

In the case of estrogen-dependent cancers, the term "effective amount" means the amount of compound of the instant invention which is capable of alleviating, ameliorating, inhibiting cancer growth, treating, or preventing the cancer and/or its symptoms in mammals, including humans.

By "pharmaceutically acceptable formulation" it is meant that the carrier, diluent, excipients and salt must be compatible with the active ingredient (a compound of formula I) of the formulation, and not be deleterious to the recipient thereof. Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be: pills, tablets, powders, lozenges, syrups, aerosols, saches, cachets, elixirs, suspensions, emulsions, ointments, suppositories, sterile injectable solutions, or sterile packaged powders, and the like, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The particular dosage of a compound of formula I required to treat, inhibit, or prevent the symptoms and/ or disease of a mammal, including humans, suffering from the above maladies according to this invention will depend upon the particular disease, symptoms, and severity. Dosage, routes of administration, and frequency of dosing is best decided by the attending physician. Generally, accepted and effective doses will be from 15mg to 1000 mg, and more typically from 15mg to 80mg, from one to three times per day. Such dosages will be administered to a patient in need thereof, for at least one month, and typically for six months, or chronically.

The formulations which follow are given for purposes of illustration and are not intended to be limiting in any way. The total active ingredients in such formulations comprises from 0.1% to 99.9% by weight of the formulation. The term "active ingredient" means a compound of formula I.

Formulation 1: Gelatin Capsules

| Ingredient | Quantity (mg/capsule) |
| --- | --- |
| Active Ingredient | 0.1–1000 |
| Starch NF | 0–500 |

-continued

| Ingredient | Quantity (mg/capsule) |
| --- | --- |
| Starch flowable powder | 0–500 |
| Silicone fluid 350 centistokes | 0–15 |

The ingredients are blended, passed through a No. 45 mesh U.S. sieve, and filled into hard gelatin capsules.

Formulation 2: Tablets

| Ingredient | Quantity (mg/tablet) |
| --- | --- |
| Active Ingredient | 2.5–1000 |
| Starch | 10–50 |
| Cellulose, microcrystalline | 10–20 |
| Polyvinylpyrrolidone (as 10% solution in water) | 5 |
| Sodium carboxymethylcellulose | 5 |
| Magnesium stearate | 1 |
| Talc | 1–5 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules thus produced are dried at 50°–60° C. and passed through a No. 18 mesh U.S. sieve. The sodium carboxymethylcellulose, magnesium stearate, and talc, previously passed through a No. 60 mesh U.S. sieve, are added to the above granules and thoroughly mixed. The resultant material is compressed in a tablet forming machine to yield the tablets.

Formulation 3: Aerosol

| Ingredient | Weight % |
| --- | --- |
| Active Ingredient | 0.25 |
| Ethanol | 29.75 |
| Propellant 22 | 70.00 |
| (Chlorodifluoromethane) | |
| Total | 100.00 |

The active ingredient is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Suppositories

| Ingredient | Weight |
| --- | --- |
| Active ingredient | 150 mg |
| Saturated fatty acid glycerides | 3000 mg |

The active ingredient is passed through a No. 60 mesh U.S. sieve and suspended in the fatty acid glycerides which had previously heated to their melting point. The mixture is poured into a suppository mold and allowed to cool.

Formulation 5: Suspension

Suspensions each containing 0.1–1000 mg of a compound of formula I per 5 mL dose.

| Ingredient | Weight |
| --- | --- |
| Active Ingredient | 0.1–1000 mg |
| Sodium carboxymethyl cellulose | 50 mg |
| Syrup | 1.25 mL |
| Benzoic acid solution (0.1 M) | 0.10 mL |
| Flavor | q.v. |
| Color | q.v. |
| Purified water to total | Total 5 mL |

A compound of formula I is passed through a No. 45 mesh U.S. sieve and mixed with the sodium carboxymethyl cellulose and syrup to form a smooth paste. The benzoic acid solution, flavor, and color diluted in water are added and mixture stirred thoroughly. Additional water is added to bring the formulation to final volume.

The following Examples and Preparations are provided to better elucidate the practice of the instant invention and should not be interpreted in any way as to limit the scope of same. Those skilled in the art will recognize that various modifications may be made while not departing from the spirit and scope of the invention. All publications and patent applications mentioned in the specification are indicative of the level of those skilled in the art to which this invention pertains.

NMR data for the following Examples were generated on a GE 300 MHz NMR instrument, and anhydrous $CDCl_3$ was used as the solvent unless otherwise indicated. Field strength for $^{13}C$ NMR spectra was 75.5 MHz, unless otherwise indicated.

EXAMPLES

Preparation 1

2-(4-Methoxyphenyl)-3-bromo-6-methoxybenzo[b]thiophene

To a solution of 2-(4-methoxyphenyl)-6-methoxybenzo[b]thiophene (27.0 g, 100 mmol) in 1.10 L of chloroform at 60° C. was added bromine (15.98 g, 100 mmol) dropwise dissolved in 200 mL of chloroform. After the addition was complete, the reaction was cooled to room temperature, and the solvent removed in vacuo to provide 34.2 g (100%) of 2-(4-methoxyphenyl)-3-bromo-6-methoxybenzo[b]thiophene as a white solid. mp 83°–850 C. $^1H$ NMR (DMSO-$d_6$) $\delta$7.70–7.62 (m, 4H), 7.17 (dd, J=8.6, 2.0 Hz, 1H), 7.09 (d, J=8.4 Hz, 2H). FD mass spec: 349, 350. Anal. Calcd. for $C_{16}H_{13}BrO_2S$: C, 55.03; H, 3.75. Found: C, 54.79; H, 3.76.

Preparation 2

2-(4-Methoxyphenyl)-3-[N-(4-benzyloxyphenyl)acetamido]-6-methoxy-benzo[b]thiophene To a solution of 2-(4-methoxyphenyl)-3-bromo-6-methoxybenzo[b]thiophene (34.20 g, 0.098 mol) and N-4-benzyloxyphenylacetamide (23.7 g, 0.098 mol) in 100 mL of 2,4,6-collidine under $N_2$ was added $Cu_2O$ (14.0 g, 0.098 mol). The resulting mixture was heated to reflux for 72 h. Upon cooling, the reaction was diluted with $CH_2Cl_2$ and the precipated solids were removed by filtration. The filtrate was concentrated in vacuo, and the residue dissolved in EtOAc. The organic was then extracted several times with 5.0 N HCl. The organic was dried ($Na_2SO_4$) and concentrated in vacuo to a solid. Chromatography ($SiO_2$, $CHCl_3$) provided 2.43 g (5%) of 2-(4-methoxyphenyl)-3-[N-(4-benzyloxyphenyl)acetamido]-6-methoxy-benzo[b]thiophene as an amber foam. $^1H$ NMR (DMSO-$d_6$) $\delta$(doubling due to amide rotamers) 7.70–6.80 (m, 16H), 4.90 (bs, 2H), 3.78–3.75 (m, 6H), 2.11 and 1,78 (s, 3H). FD mass spec: 509.

Preparation 3

2-(4-Methoxyphenyl)-3-[N-(4-hydroxyphenyl)acetamido]-6-methoxy-benzo[b]thiophene 2-(4-Methoxyphenyl)-3-[N-(4-benzyloxyphenyl)acetamido]-6-methoxy-benzo[b]thiophene (2.43 g, 4.77 mmol) was dissolved in 50 mL of 1:1 EtOH/EtOAc containing 5% con. HCl. To this solution was added 1.0 g of 5% Pd/C. The resulting mixture was hydrogenated at 40 psi for 4 h. The mixture was then filtered through Celite to remove the catalyst. The filtrate was concentrated in vacuo to a semi-solid. Chromatography ($SiO_2$, $CHl_3$) provided 1.32 g (83%) of 2-(4-methoxyphenyl)-3-[N-(4-hydroxyphenyl)acetamido]-6-methoxy-benzo[b]thiophene as an amber foam. $^1H$ NMR (DMSO-$d_6$) $\delta$ (doubling due to amide rotamers) 9.53 and 9.36 (s, 1H), 7.62–6.51 (m, 11 H), 3.78 and 3.58 (s, 6H), 2.01 and 1.76 (s, 3H). FD mass spec: 419. Anal. Calcd. for $C_{24}H_{21}NO_4S.O$ 0.19 $CHCl_3$: C, 65.71; H, 4.83; N, 3.17. Found: C, 65.80; H, 4.70; N, 3.01.

Example 1

2-(4-Methoxyphenyl)-3-[N-[4-[2-(1-piperidinyl)ethoxy]phenyl]acetamido]-6-methoxybenzo[b]thiophene To a solution of 2-(4-methoxyphenyl)-3-[N-(4-hydroxyphenyl)acetamido]-6-methoxy-benzo[b]thiophene (1.31 g, 3.13 mmol) and $Cs_2CO_3$ (4.10 g, 12.50 mmol) in 15 mL of anhydrous DMF was added 2-chlorethylpiperidine hydrochloride (1.15 g, 6.26 mmol). The resulting mixture was stirred vigorously at room temperature for 5 h. The reaction mixture was diluted with 200 mL of $H_2O$, and then extracted several times with EtOAc. The combined organic was then washed with $H_2O$ several times and then dried ($Na_2SO_4$), Concentration in vacuo provided an oil. Chromatography (1% $CH_3OH/CHCl_3$, $SiO_2$) provided 1.49 g (90%) of 2-(4-methoxyphenyl-3-[N-[4-[2-(1-piperidinyl)ethoxy]phenyl]acetamido]-6-methoxybenzo[b]thiophene as an amber oil. $^1H$ NMR (DMSO-$d_6$) $\delta$ (doubling due to amide rotamers) 7.66–6.70 (m, 11 H), 3.93 (m, 2H) 3.78 and 3.58 (s, 6H), 2.8–2.30 (m, 6H), 2.01 and 1.78 (s, 3H), 1.52–1.11 (m, 6H). FD mass spec: 530. Anal. Calcd. for $C_{31}H_{34}N_2O_4S$: C, 70.16; H, 6.46; N, 5.28. Found: C, 70.33; H, 6.34; N, 5.35.

Example 2

2-(4-Methoxyphenyl)-3-[N-[4-[2-(1-piperidinyl)ethoxy]phenyl]amino]-6-methoxybenzo[b]thiophene Di-Hydrochloride To a solution of 2-(4-methoxyphenyl-3-[N-[4-[2-(1-piperidinyl)ethoxy]phenyl]acetamido]-6-methoxybenzo[b]thiophene 1.49 g, 2.80 mmol) in 10 mL of absolute EtOH was added 10 mL of 50% NaOH solution. The resulting mixture was heated to reflux for 18 h. Upon cooling, the mixture was diluted with 200 mL of $H_2O$. The aqueous was then extracted with EtOAc (3×100 mL). The organic was combined, washed with brine, then dried ($Na_2SO_4$). Concentration in vacuo provided a foam that was chromatographed ($CHCl_3$, $SiO_2$). The isolated oil was converted to the hydrochloride salt by treatment with $Et_2O.HCl$ in EtOAc. Isolation by filtration provided 1.37 g (100%) of 2-(4-methoxyphenyl)-3-[N-[4-[2-(1-piperidinyl)ethoxy]phenyl]amino]-6-methoxybenzo[b]thiophene hydrochloride as a white solid. mp 126°–130° C. $^1$H NMR (DMSO-$d_6$) δ7.54 (d, J=8.8 Hz, 2H), 7.48 (d, J=2.2 Hz, 1H), 7.29 (d, J=8.9 Hz, 1H), 6.92 (d, J =8.8 Hz, 2H), 6.91 (dd, J=8.9, 2.2 Hz, 1H), 6.73 (d, J=8.9 Hz, 2H), 6.50 (d, J=8.9 Hz, 2H), 4.21 (t, J=4.7 Hz, 2H), 3.78 (s, 3H), 3.71 (s, 3H), 3.43–3.31 (m, 4H), 2.97–2.90 (m, 2H), 1.80–1.61 (m, 5H), 1.35 (m, 1H). FD mass spec: 488. Anal. Calcd. for $C_{29}H_{34}N_2O_3S \cdot 2.0$ HCl: C, 62.03; H, 6.10; N, 4.99. Found: C, 61.79; H, 6.35; N, 5.27.

Example 3

2-(4-Hydroxyphenyl)-3-[N-[4-[2-(1-piperidinyl)ethoxy]phenyl]amino]-6-hydroxybenzo[b]thiophene Hydrochloride To a solution of 2-(4-methoxyphenyl)-3-[N-[4-[2-(1-piperidinyl)ethoxy]phenyl]amino]-6-methoxybenzo[b]thiophene hydrochloride (0.70 g, 1.25 mmol) in 40 mL of anhydrous $CH_2Cl_2$ under $N_2$ 10° C. was added $BBr_3$ (0.36 mL, 3.80 mmol). The solution was allowed to gradually warm to room temperature and stirred for a total of 6 h. The reaction was quenched by pouring the mixture into an excess of sat. $NaHCO_3$ solution. The aqueous was then extracted several times with 5% EtOH/EtOAc. The organic was combined and dried ($Na_2SO_4$) and then concentrated in vacuo to a foam. The crude product was chromatographed (1–6% $CH_3OH/CHCl_3$) to provide 325 mg (49%) of 2-(4-hydroxyphenyl)-3-[N-[4-[2-(1-piperidinyl)ethoxy]phenyl]amino]-6-hydroxybenzo[b]thiophene as an oil. This material was converted to the hydrochloride salt by treatment with $Et_2O.$-HCl in EtOAc, and isolated as a white solid by filtration. Data for 2-(4-Hydroxyphenyl)-3-[N-[4-[2-(1-piperidinyl)ethoxy]phenyl]amino]-6-hydroxybenzo[b]thiophene Hydrochloride: mp 140°–150° C. $^1$H NMR (DMSO-$d_6$) δ6 9.57 (s, 2H), 7.40 (d, J=8.6 Hz, 2H), 7.19 (d, J=10.1 Hz, 1H), 7.16 (d, J=2.0 Hz, 1H), 6.75 (dd, J=10.1, 2.0 Hz, 1H), 6.70 (d, J=8.6 Hz, 2H), 6.64 (d, J=8.8 Hz, 2H), 6.46 (d, J=8.8 Hz, 2H), 4.21 (m, 2H), 3.50–3.30 (m, 4H), 3.01–2.95 (m, 2H), 1.81–1.63 (m, 5H), 1.38 (m, 1H). FD mass spec: 461. Anal. Calcd. for $C_{27}H_{28}N_2O_3S \cdot 1.5$ HCl: C, 62.94; H, 5.77; N, 5.44. Found: C, 62.99; H, 5.88; N, 5.27.

Test Procedures

In the examples illustrating the methods, a postmenopausal model was used in which effects of different treatments upon circulating lipids were determined.

Seventy-five day old female Sprague Dawley rats (weight range of 200 to 225g) were obtained from Charles River Laboratories (Portage, Mich.). The animals were either bilaterally ovariectomized (OVX) or exposed to a Sham surgical procedure at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2°±1.70° C. with a minimum relative humidity of 40%. The photoperiod in the room was 12 hours light and 12 hours dark.

Dosing Regimen Tissue Collection

After a one week acclimation period (therefore, two weeks post-OVX) daily dosing with test compound was initiated. 17a -ethynyl estradiol or the test compound were given orally, unless otherwise stated, as a suspension in 1% carboxymethylcellulose or dissolved in 20% cyclodextrin. Animals were dosed daily for 4 days. Following the dosing regimen, animals were weighed and anesthetized with a ketamine: xylazine (2:1, V:V) mixture and a blood sample was collected by cardiac puncture. The animals were then sacrificed by asphyxiation with $CO_2$, the uterus was removed through a midline incision, and a wet uterine weight was determined.

Cholesterol Analysis

Blood samples were allowed to clot at room temperature for 2 hours, and serum was obtained following centrifugation for 10 minutes at 3000 rpm. Serum cholesterol was determined using a Boehringer Mannheim Diagnostics high performance cholesterol assay. Briefly the cholesterol was oxidized to cholest-4-en-3-one and hydrogen peroxide. The hydrogen peroxide was then reacted with phenol and 4-aminophenazone in the presence of peroxidase to produce a p-quinone imine dye, which was read spectrophotemetrically at 500 nm. Cholesterol concentration was then calculated against a standard curve. The entire assay was automated using a Biomek Automated Workstation.

Uterine Eosinophil Peroxidase (EPO) Assay

Uteri were kept at 4° C. until time of enzymatic analysis. The uteri were then homogenized in 50 volumes of 50 mM Tris buffer (pH -8.0) containing 0.005% Triton X-100. Upon addition of 0.01% hydrogen peroxide and 10 mM 0-phenylenediamine (final concentrations) in Tris buffer, increase in absorbance was monitored for one minute at 450 nm. The presence of eosonophils in the uterus is an indication of estrogenic activity of a compound. The maximal velocity of a 15 second interval was determined over the initial, linear portion of the reaction curve.

Source of Compound 17a-ethynyl estradiol was obtained from Sigma Chemical Co., St. Louis, Mo.

Influence of Formula I Compounds on Serum Cholesterol and Determination of Agonist/Non-Agonist Activity Data presented in Table 1 below show comparative results among ovariectomized rats, rats treated with 17a-ethynyl estradiol ($EE_2$; an orally available form of estrogen), and rats treated with certain compounds of the instant invention. Although $EE_2$ caused a decrease in serum cholesterol when orally administered at 0.1 mg/kg/day, it also exerted a stimulatory action on the uterus so that $EE_2$ uterine weight was substantially greater than the uterine weight of ovariectomized test animals. This uterine response to estrogen is well recognized in the art.

Not only did the compounds of the instant invention generally reduce serum cholesterol compared to the ovariectomized control animals, but uterine weight was only minimally increased to slightly decreased with the majority of the formula compounds tested. Compared to estrogenic compounds known in the art, the benefit of serum cholesterol reduction without adversely affecting uterine weight is quite rare and desirable.

As is expressed in the data below, estrogenicity also was assessed by evaluating the adverse response of eosinophil infiltration into the uterus. The compounds of the instant invention did not cause any increase in the number of eosinophils observed in the stromal layer of ovariectomized rats, while estradiol cause a substantial, expected increase in eosinophil infiltration.

The data presented in Table 1 below reflects the response of 5 to 6 rats per treatment.

TABLE 1

| Compound No. | Dose mg/kg[a] | Uterine Weight % Inc[b] | Uterine Eosinophil (Vmax)[c] | Serum Cholest. % Dec.[d] |
|---|---|---|---|---|
| EE2[e] | 0.1 | 124.4* | 85.5* | 78.1* |
| Example 2 | 0.1 | 55.4* | 10.2 | 42.8* |
|  | 1.0 | 89.5* | 12.9 | 46.4* |
|  | 10. | 86.3* | 6.6 | 66.8* |
| Example 3 | 0.1 | 45.2* | 1.2 | 63.0* |
|  | 1.0 | 39.4* | 4.5 | 51.7* |
|  | 10.0 | 35.0* | 4.8 | 64.9* |

[a]mg/kg PO
[b]Uterine Weight % increase versus the ovariectomized controls
[c]Eosinophil peroxidase Vmax
[d]Serum cholesterol decrease versus ovariectomized controls
[e]17-a-Ethynyl-estradiol
*p<.05

In addition to the demonstrated benefits of the compounds of the instant invention, the above data clearly demonstrate that compounds of Formula I are not estrogen mimetics. Furthermore, no deleterious toxicological effects (for example, survival numbers) were observed with any treatment.

Osteoporosis Test Procedure

Following the General Preparation Procedure, infra, the rats are treated daily for 35 days (6 rats per treatment group) and sacrificed by carbon dioxide asphyxiation on the 36th day. The 35 day time period is sufficient to allow maximal reduction in bone density, measured as described herein. At the time of sacrifice, the uteri are removed, dissected free of extraneous tissue, and the fluid contents were expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitilized x-rays generated and analyzed by an image analysis program (NIH image) at the distal metaphysis. The proximal aspect of the tibiae from these animals are also scanned by quantitative computed tomography.

In accordance with the above procedures, compounds of the instant invention and ethynyl estradiol (EE$_2$) in 20% hydroxypropyl β-cyclodextrin are orally administered to test animals. Distal femur metaphysis and proximal tibiae data results are reported as percent protection relative to ovariectomy.

In summary, ovariectomy of the test animals caused a significant reduction in femur density compared to intact, vehicle treated controls. Orally administered ethynyl estradiol (EE2) prevents this loss, but the risk of uterine stimulation with this treatment is ever-present.

The compounds of the instant invention also prevent bone loss in a general, dose-dependent manner. Accordingly, the compounds of the instant invention are useful for the treatment of osteoporosis, particularly caused by postmenopausal syndrome.

We claim:
1. A compound of formula I formula I

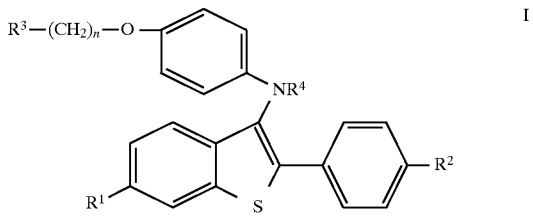

wherein:
R$^1$ is —H, —OH, —O(C$_1$-C$_4$ alkyl), —OCOAr, —(CO)OAr, where Ar is phenyl or substituted phenyl, —OCO(C$_1$-C$_6$ alkyl), —O(CO)O(C$_1$-C$_6$ alkyl), or —OSO$_2$(C$_2$-C$_6$ alkyl);

R$^2$ is —H, —Cl, —F, —OH, —O(C$_1$-C$_4$ alkyl), —OCOAr, —O(CO)OAr, where Ar is phenyl or substituted phenyl, —OCO(C$_1$-C$_6$ alkyl), —O(CO)O(C$_1$-C$_6$ alkyl), or —OSO$_2$(C$_2$-C$_6$ alkyl);

R$^3$ is 1-piperidinyl, 1-pyrrolidinyl, methyl-1-pyrrolidinyl, dimethyl-1-pyrrolidinyl, 4-morpholino, dimethylamino, diethylamino, diisopropylamino, or 1-hexamethyleneimino;

R$^4$ is —H, C$_1$-C$_5$ alkyl, —COAr, —(CO)H, —CO(C$_1$-C$_6$ alkyl), —SO$_2$(C$_2$-C$_6$ alkyl), or —SO$_2$Ar, where Ar is phenyl or substituted phenyl; and n is 2 or 3; or a pharmaceutically acceptable salt or solvate thereof.

2. A compound according to claim 1 wherein R$^4$ is —H.
3. A compound according to claim 1 wherein R$^4$ is —COCH$_3$.
4. A compound according to claim 1 wherein R$^1$ and R$^2$ each are —OH.
5. A compound according to claim 1 wherein R$^1$ and R$^2$ each are —OCH$_3$.
6. A compound according to claim 1 wherein n is 2.
7. A compound according to claim 1 wherein R$^3$ is 1-piperidinyl.
8. A compound according to claim 7 wherein said salt thereof is the hydrochloride salt.
9. A compound according to claim 1 selected from the group consisting of
2-(4-methoxyphenyl)-3-[N-[4-[2-(1-piperidinyl)ethoxy]phenyl]acetamido]-6-methoxybenzo[b]thiophene;
2-(4-hydroxyphenyl)-3-[N-[4-[2-(1-piperidinyl)ethoxy]phenyl]acetamido]-6-hydroxybenzo[b]thiophene;
2-(4-methoxyphenyl)-3-[N-[4-[2-(1-piperidinyl)ethoxy]phenyl]acetamido]-6-hydroxybenzo[b]thiophene;
2-(4-hydroxyphenyl)-3-[N-[4-[2-(1-piperidinyl)ethoxy]phenyl]amino]-6-methoxybenzo[b]thiophene;
2-(4-methoxyphenyl)-3-[N-[4-[2-(1-piperidinyl)ethoxy]phenyl]-N-ethylamino]-6-methoxybenzo[b]thiophene;
2-(4-Methoxyphenyl)-3-[N-[4-[2-(1-piperidinyl)ethoxy]phenyl]propanoylamido]-6-methoxybenzo[b]thiophene;
2-(4-methoxyphenyl)-3-[N-[4-[2-(1-piperidinyl)ethoxy]phenyl]acetamido]-6-methoxybenzo[b]thiophene;
2-(4-methoxyphenyl)-3-[N-[4-[3-(1-piperidinyl)propoxy]phenyl]acetamido]benzo[b]thiophene;
2-(4-methoxyphenyl)-3-[N-[4-[2-(1-piperidinyl)ethoxy]phenyl]acetamido]-6-methoxybenzo[b]thiophene;
2-(4-methoxyphenyl)-3-[N-[4-[2-(1-pyrrolidinyl)ethoxy]phenyl]amino]-6-methoxybenzo[b]thiophene;
2-(4-chlorophenyl)-3-[N-[4-[3-(1-hexamethylene)propoxy]phenyl]butanoylimido]-6-methoxybenzo[b]thiophene;
2-phenyl-3-[N-[4-[2-(1-piperidinyl)ethoxy]phenyl]-N-methylamino]benzo[b]thiophene;

2-(4-chlorophenyl)-3-[N-[4-[3-(1-pyrrolidinyl)propoxy] phenyl]-N-butylamino]-6-hydroxybenzo[b]thiophene;

2-(4-acetyloxyphenyl)-3-[N-[4-[2-(1-piperidinyl)ethoxy] phenyl]acetamido]-6-methoxybenzo[b]thiophene;

2-(4-methoxyphenyl)-3-[N-[4-[2-(1-piperidinyl)ethoxy] phenyl]acetamido]-6-n-butylsulfonyloxybenzo[b] thiophene;

2-phenyl-3-[N-[4-[2-(1-piperidinyl)ethoxy]phenyl] acetamido]-6-benzoyloxybenzo[b]thiophene;

2-(4-benzoyloxyphenyl)-3-[N-[4-[3-(1-piperidinyl) propoxy]phenyl]acetamido]-6-methoxybenzo[b] thiophene;

2-(4-benzoyloxyphenyl)-3-[N-[4-[3-(1-hexamethyleneimino)propoxy]phenyl]-N-2-butylamino]-6-methoxybenzo[b]thiophene; and 2-[4-(4-methoxybenzoyloxy)phenyl]-3-[N-[4-[2-(1-piperidinyl)ethoxy]phenyl]-N-methylamino]-6-methoxybenzo[b]thiophene.

10. A pharmaceutical formulation comprising a compound of claim 1 and one or more pharmaceutically acceptable carriers, solvents, or diluents.

11. A method of inhibiting bone loss or bone resorption which comprises administering to a patient in need thereof an effective amount of a compound of claim 1.

12. A method according to claim 11, wherein said bone loss or bone resorption is due to menopause or ovariectomy.

13. A method of lowering serum cholesterol levels which comprises administering to a patient in need thereof an effective amount of a compound of claim 1.

* * * * *

UNITED STATES PATENT AND TRADEMARK OFFICE
CERTIFICATE OF CORRECTION

PATENT NO. : 5,843,963
DATED : December 1, 1998
INVENTOR(S) : Kenneth Lee Hauser, Alan Palkowitz, Kenneth Jeff Thrasher It is certified that error appears in the above-indentified patent and that said Letters Patent is hereby corrected as shown below:

On the title page, item [60]:
delete "60/026,556" and insert in replacement thereof, -- 60/026,557 --.

In column 1, line 7, delete "60/026,556" and insert in replacement thereof, -- 60/026,557 --.

Signed and Sealed this

Twenty-sixth Day of October, 1999

*Attest:*

Q. TODD DICKINSON

*Attesting Officer*    *Acting Commissioner of Patents and Trademarks*

UNITED STATES PATENT AND TRADEMARK OFFICE
CERTIFICATE OF CORRECTION

PATENT NO. : 5,843,963

DATED : December 1, 1998

INVENTOR(S) : Kenneth Lee Hauser, Alan Palkowitz, Kenneth Jeff Thrasher

It is certified that error appears in the above-identified patent and that said Letters Patent is hereby corrected as shown below:

In column 22, line 13 should read "$R^1$ is -H, -OH, -O($C_1$-$C_4$ alkyl),-OCOAr, -O(CO)".

Signed and Sealed this

Eleventh Day of April, 2000

Attest:

Q. TODD DICKINSON

Attesting Officer

Director of Patents and Trademarks